United States Patent [19]
Kim

[11] Patent Number: 6,018,681
[45] Date of Patent: Jan. 25, 2000

[54] IMPLANTABLE ATRIAL DEFIBRILLATOR HAVING THERAPY INHIBITION RESPONSIVE TO ATRIAL CYCLE LENGTH

[75] Inventor: Jaeho Kim, Redmond, Wash.

[73] Assignee: InControl, Inc., Redmond, Wash.

[21] Appl. No.: 08/984,588

[22] Filed: Dec. 3, 1997

[51] Int. Cl.⁷ ................................................. A61N 1/39
[52] U.S. Cl. ................................................................ 607/5
[58] Field of Search ..................... 607/4, 5, 14; 600/515, 600/516–519

[56] References Cited

U.S. PATENT DOCUMENTS

| | | | |
|---|---|---|---|
| 5,205,283 | 4/1993 | Olson | 600/518 |
| 5,486,199 | 1/1996 | Kim et al. | 600/518 |
| 5,554,175 | 9/1996 | Alferness et al. | 607/5 |

*Primary Examiner*—William E. Kamm
*Assistant Examiner*—Kennedy J. Schaetzle
*Attorney, Agent, or Firm*—Richard O. Gray, Jr.

[57] ABSTRACT

There is disclosed an atrial defibrillator including a lead system for sensing activity of a heart in or near at least on atrium of the heart, a detector for detecting atrial events from the sensed atrial activity, and a cardioverter for applying cardioverting electrical energy to the atria of the heart when the atria are in need of cardioversion. A timer determines time spans between successive detected atrial events and an inhibit stage precludes the cardioverter from applying cardioverting energy to the heart when a time span is greater than a predetermined limit.

6 Claims, 1 Drawing Sheet

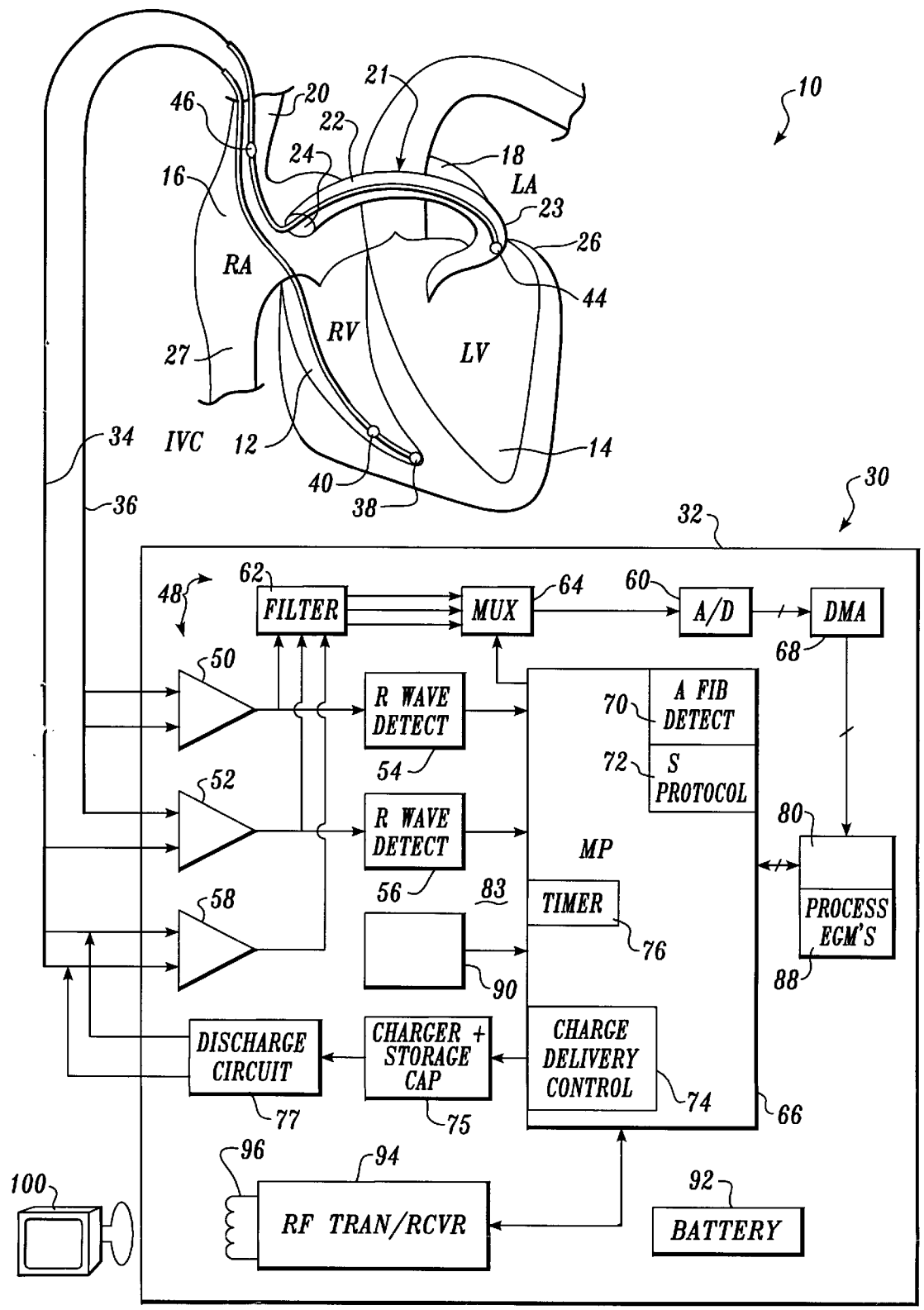

IMPLANTABLE ATRIAL DEFIBRILLATOR HAVING THERAPY INHIBITION RESPONSIVE TO ATRIAL CYCLE LENGTH

BACKGROUND OF THE INVENTION

The present invention generally relates to an automatic implantable atrial defibrillator for delivering cardioverting or defibrillating electrical energy to the atria of a human heart. The present invention is more particularly directed to such an atrial defibrillator which inhibits therapy delivery when the time span between detected atrial events exceeds a predetermined limit to avoid delivering therapy when the heart reverts to normal sinus rhythm or during a normal sinus rhythm cycle of the heart.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Early implantable atrial defibrillators were proposed to provide patients suffering from occurrences of atrial fibrillation with relief. Unfortunately, to the detriment of such patients, these early atrial defibrillators never became a commercial reality.

Two such proposed defibrillators, although represented as being implantable, were not fully automatic, requiring human interaction for cardioverting or defibrillating the heart. Both of these proposed defibrillators required the patient to recognize the symptoms of atrial fibrillation. One defibrillator required a visit to a physician for activation of the defibrillator and the other defibrillator required the patient to activate the defibrillator from external to the patient's skin with a magnet.

An improved atrial defibrillator which provides automatic operation is fully disclosed in U.S. Pat. No. 5,282,837 entitled "IMPROVED ATRIAL DEFIBRILLATOR AND METHOD," and which issued on Feb. 1, 1994 in the names of John M. Adams and Clifton A. Alferness. This patent is assigned to the assignee of the present invention and is incorporated herein by reference.

In addition to being automatic in operation, the atrial defibrillator of the above-referenced patent includes further features to assure the safe operation of the device. For example, to assure that the cardioverting electrical energy is not applied during the T wave vulnerable period of the heart, the atrial defibrillator provides R wave detection of increased reliability which is utilized to advantage in synchronizing the delivery of the cardioverting electrical energy to the atria with an R wave of the heart. Further, as another feature, an electrode system is utilized which minimizes the amount of energy that is required to cardiovert the atria. This is achieved by locating the cardioverting electrodes in or near the atria of the heart to provide a cardioverting energy path which confines substantially all of the cardioverting electrical energy to the atria of the heart.

Further improvements directed to the safe operation of an implantable automatic atrial defibrillator are described in U.S. Pat. No. 5,207,219 which issued on May 4, 1993 for "ATRIAL DEFIBRILLATOR AND METHOD FOR PROVIDING INTERVAL TIMING PRIOR TO CARDIOVERSION," and which is also assigned to the assignee of the present invention and incorporated herein by reference. The atrial defibrillator there disclosed provides an answer to the observation that during episodes of atrial fibrillation, the cardiac rate increases to a high rate and/or becomes extremely variable. At high or variable cardiac rates, the R wave of a cardiac cycle may become closely spaced from the T wave of the immediately preceding cardiac cycle. This creates a condition known in the art as an "R on T" condition which is believed to contribute to induced ventricular fibrillation if the atria are cardioverted in synchronism with the R wave close to the preceding T wave. In order to prevent cardioversion of the atria during an R on T condition, the atrial defibrillator described in U.S. Pat. No. 5,207,219 detects for a cardiac interval longer than a minimum interval prior to delivering the cardioverting electrical energy to the atria. This assures that the cardioverting electrical energy is not delivered during an R on T condition.

In addition to the foregoing, there is certain electrogram data related to atrial fibrillation detection and cardioversion from which the cardiologist would benefit. Such information includes electrograms of the heart during fibrillation to confirm proper operation of the atrial fibrillation detector, electrograms of the heart prior to cardioversion and electrograms of the heart from immediately prior to and ending after the deliverance of the cardioverting electrical energy to the atria to confirm that the application of the cardioverting electrical energy was synchronized with an R wave and not on a T wave and to also confirm that the cardioversion was successful by returning the heart to normal sinus rhythm. One such implantable automatic atrial defibrillator capable of storing such electrogram data for later recall by the cardiologist is fully disclosed in U.S. Pat. No. 5,522,850 which issued on Jun. 4, 1996 for "DEFIBRILLATION AND METHOD FOR CARDIOVERTING A HEART AND STORING RELATED ACTIVITY DATA," which is assigned to the assignee the present invention, and which is incorporated herein by reference.

One problem with storing electrogram data related to the cardioversion of atrial fibrillation is that during atrial fibrillation, the heart may spontaneously convert to normal sinus rhythm or do so for at least one or more cardiac cycles. Such a cardiac cycle would most likely satisfy electrical energy therapy criteria, including a minimum interval criteria. Hence, it is possible for the defibrillator to correctly detect the presence of atrial fibrillation and then deliver cardioverting energy on cycle which, when later reviewed by the cardiologist, would appear to be a normal sinus rhythm cardiac cycle.

SUMMARY OF THE INVENTION

The invention provides an atrial defibrillator including a lead system for sensing activity of a heart in or near at least one atrium of the heart and a detector for detecting atrial events from the sensed atrial activity. The defibrillator further includes a cardioverter for applying cardioverting electrical energy to the atria of the heart when the atria are in need of cardioversion and means for determining time spans between successive detected atrial events. Inhibit means precludes the cardioverter from applying the cardioverting energy when a time span is greater than a predetermined limit.

The invention further provides an atrial cardioverter including means for sensing atrial activity of a heart, an atrial arrhythmia detector responsive to sensed atrial activity for detecting an atrial arrhythmia of the heart, and atrial therapy means for providing atrial therapy to the heart responsive to detection of an atrial arrhythmia. An atrial cycle length determining means is responsive to sensed atrial activity for inhibiting the provision of atrial therapy when an atrial cycle length exceeds a predetermined length.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the sole figure of which like reference numerals identify identical elements, and wherein the sole FIGURE is a schematic block diagram of a fully implantable atrial defibrillator/cardioverter embodying the present invention.

DETAILED DESCRIPTION OF THE PREFERRED EMBODIMENT

Referring now to FIG. 1, it illustrates an implantable automatic atrial defibrillator/cardioverter 30 embodying the present invention.

The atrial defibrillator 30 includes an implantable enclosure 32 and an implantable lead system including an intravascular lead 34 and an endocardial lead 36. The endocardial lead 36 has tip and ring electrodes 38 and 40 respectively adapted for placement in the right ventricle 12. The intravascular lead 34 has a tip electrode 44 adapted for placement in the coronary sinus 22 or the great cardiac vein 23 and a ring electrode 46 adapted for placement in the superior vena cava 20 or right atrium 16. An alternative lead system may include separate leads for electrodes 44 and 46. This requires an additional endocardial lead (not shown in FIG. 1) adapted for placing electrode 46 in the superior vena cava 20 or the right atrium 16.

Electrodes 44 and 46 of lead 34 sense atrial activity of the heart. Electrodes 44 and 46 perform the additional function of applying cardioverting electrical energy across the atria 16 and 18 of the heart.

Electrodes 38 and 40 sense R waves of the heart and may be referred to herein as the first electrode pair. Electrode 44 together with either electrode 38 or electrode 40 also sense R waves of the heart and may be referred to herein as the second electrode pair. The dual sensing of the R waves between the first and second electrode pairs is performed for the purpose of reliably sensing the R waves as fully described in U.S. Pat. No. 5,348,021, which issued on Sep. 20, 1994, for "APPARATUS AND METHOD FOR RELIABLY DETECTING A DEPOLARIZATION ACTIVATION WAVE OF THE HEART AND ATRIAL DEFIBRILLATOR UTILIZING SAME," which patent is assigned to the assigned of the present invention and incorporated herein by reference.

The implantable enclosure 32 includes a microprocessor 66 and a memory 80. The microprocessor controls the overall function of the atrial defibrillator 30 under software controlled by operating instructions stored in a memory 80. The memory 80 includes a process memory portion 88 for storing electrocardiogram data samples to be processed by the microprocessor 66 as will be described subsequently. The memory 80 further includes an episode log 86 for storing digital data representative of electrograms related to the detection and cardioversion of atrial fibrillation episodes.

Within the enclosure 32, the atrial defibrillator 30 further includes a data acquisition means 48 including sense amplifiers 50, 52, and 58, filter 62, multiplexer 64, analog-to-digital converter 60, and direct memory access controller (DMA) 68. Sense amplifier 50 is coupled to electrodes 38 and 40 of lead 36 and sense amplifier 52 is coupled to electrode 44 of lead 34 and to either electrode 38 or electrode 40 of lead 36. The sense amplifiers 50 and 52 amplify the electrogram signals provided by the first and second pairs of electrodes respectively and provide R wave detectors 54 and 56 respectively with an amplified output. The R wave detectors 54 and 56 each include a threshold circuit which isolates the R waves from the amplified electrograms provided by sense amplifiers 50 and 52. The outputs of the R wave detectors 54 and 56 are coupled to the microprocessor for conveying the isolated R waves to the microprocessor 66.

Sense amplifier 58 is coupled to electrodes 44 and 46 of lead 34. The sense amplifier 58 provides an amplified output of the electrograms sensed by the first electrode pair consisting of electrodes 44 and 46. The electrograms provided by sense amplifier 58 predominantly represent atrial activity of the heart 10.

The outputs of the sense amplifiers 50, 52 and 58 are coupled to an analog-to-digital converter 60 through the filter 62 and the multiplexer 64. The analog-to-digital converter 60 digitizes the electrograms provided by the amplifiers 50, 52 and 58 to generate electrogram digital data samples. The electrogram samples are conveyed to the direct memory access 68 which then stores the electrogram samples in memory portion 88 of memory 80.

The sense amplifier 58 is further coupled to an A wave detector 90. The A wave detector 90 preferably includes a differentiating filter 91 and a threshold circuit to provide atrial event detection. Whenever the output of sense amplifier transitions above or below a threshold set by the threshold circuit, the A wave detector will provide an output pulse. One such output pulse will indicate the beginning of an atrial event and a following output pulse may indicate the end of the atrial event. Since the electrodes 44 and 46 are widely spaced, the atrial event detection may be caused by both atrial activity and far field ventricular activity. The output pulses of the atrial event detector are conveyed to the microprocessor 66.

In controlling the function of the atrial defibrillator 30, the microprocessor 66 implements a number of stages including an atrial fibrillation detector 70, a synchronization protocal stage 72, an inhibit stage 73, a charge and delivery control stage 74, a timer 76, a counter 78, and an enable stage 79.

At spaced apart predetermined times or when there is a probability of atrial fibrillation as taught in U.S. Pat. No. 5,282,837 which issued on Feb. 1, 1994 for ATRIAL DEFIBRILLATOR AND METHOD and incorporated herein by reference, the atrial fibrillation detector 70 is enabled to determine if the heart 10 is in atrial fibrillation. To that end, a segment of electrogram digital data (for example an eight second segment) from amplifiers 50 and 58 is first stored in memory portion 88. The microprocessor then accesses that data when implementing the atrial fibrillation detector 70 to determine if the atria are in fibrillation. The atrial fibrillation detector may be implemented as disclosed in U.S. Pat. No. 5,522,852 which issued on Jun. 4, 1996 for "SELECTIVE CARDIAC ACTIVITY ANALYSIS ATRIAL FIBRILLATION DETECTION SYSTEM AND METHOD AND ATRIAL DEFIBRILLATOR UTILIZING SAME," and/or U.S. Pat. No. 5,486,199 which issued on Jan. 23, 1996 for "SYSTEM AND METHOD FOR REDUCING FALSE POSITIVES IN ATRIAL FIBRILLATION DETECTION," which patents are assigned to the assignee of the present invention and incorporated herein by reference.

When cardioversion is required, the microprocessor 66, under software control pursuant to operating instructions obtained from the memory 80, implements the charge and delivery control 74. The charge and delivery control 74 first causes the charger of circuit 75 to charge the storage capacitor therein to a selected peak voltage. The charge and delivery control 74 monitors the charging of the capacitor. When the charge delivery control 74 determines that the voltage across the storage capacitor has reached a selected peak voltage, the microprocessor, through the charge and delivery control 74, terminates the charging.

After the charging of the storage capacitor is completed, the microprocessor implements the synchronization protocol stage 72. The stage 72 obtains electrogram data from the DMA 68 to confirm that R waves are being reliably sensed, and that certain morphological characteristics of the heart are met. The stage 72 also detects for a cardiac interval which is longer than a preselected minimum time interval. Such synchronization criteria is fully described in U.S. Pat. No. 5,207,219, which issued on May 4, 1993, for "ATRIAL DEFIBRILLATOR AND METHOD FOR PROVIDING INTERVAL TIMING PRIOR TO CARDIOVERSION," and U.S. Pat. No. 5,584,864 which issued on Dec. 17, 1996 for "CARDIOVERSION SYNCHRONIZATION SYSTEM AND METHOD FOR AN ATRIAL DEFIBRILLATOR." Both patents are assigned to the assignee of the present invention and incorporated herein by reference.

Upon the successful completion of the synchronization protocol, the charge and delivery control 74 causes a discharge circuit 77, which is coupled to the storage capacitor of circuit 75, to discharge a portion of the energy stored in the storage capacitor. The discharged energy is applied to electrodes 44 and 46 of the intravascular lead 34 for applying the cardioverting electrical energy to the atria 16 and 18 of the heart 10. The discharged energy is preferably applied in synchronism with a detected ventricular activation or R wave.

Lastly, the atrial defibrillator 30 includes an RF transmitter/receiver 94 within enclosure 32. The RF transmitter/receiver includes a coiled antenna 96 for communicating through telemetry to an external programmer 100. The telemetry link provided by the RF transmitter/receiver 94 and the external programmer 100 permits the cardiologist to program the atrial defibrillator 30 with respect to its various programmable parameters and to enable the cardiologist to read from the atrial defibrillator 30 certain data which has been stored in the episode log 86 of memory 80.

In accordance with the present invention, after the storage capacitor of circuit 75 is charged to a desired peak voltage, and as the synchronization stage 72 function to identify a suitable R wave upon which to provide the atrial cardioverting therapy, the A wave detector 90 continues to detect atrial events. The timer 76 times the time space between successive atrial events to determine the atrial cycle length between successive detected atrial events. If a time span or atrial cycle length is greater than a predetermined limit, the present cardiac cycle is considered to be a normal sinus rhythm cardiac cycle. Responsive to such a determination by timer 76, the inhibit 73 will inhibit the charge and delivery control stage 74 from applying cardioverting energy to the heart during the present cardiac cycle. If it is desired to apply the cardioverting energy synchronized to an R wave, then, if timer 76 determines that the length of a just completed atrial cycle exceeds the limit, the inhibit stage 73 will inhibit therapy and not permit a cardioversion attempt on the next detected R wave.

The atrial cycle length predetermined limit may be, for example, on the order of five hundred milliseconds. Atrial cycle lengths exceeding five hundred milliseconds, for example, would therefore denote normal sinus rhythm during the present cardiac cycle to cause the therapy delivery to be inhibited.

As previously mentioned, the A wave detector 90, for each detected atrial event, provides at least a first pulse to denote the beginning of an atrial event and preferably a last pulse to denote the end of the atrial event. This enables the timer 76 to preferably time each time span or atrial cycle length from the beginning of an atrial event to the beginning of an immediately successive atrial event.

The counter 78 is incremented each time the inhibit stage 73 inhibits therapy delivery. In accordance with further aspects of the present invention, when the counter 78 reaches a preselected count, such as three, for example, the synchronization stage 72 is caused to pause and the enable stage 79 causes the atrial fibrillation detector to redetect for atrial fibrillation. This function is provided because if three atrial event cycle lengths which exceed the predetermined limit are detected before therapy is delivered, it may well be that the heart has spontaneously converted to normal sinus rhythm rendering therapy delivery unnecessary. This also helps to conserve the power of the battery 92 and leads to extending the useful life of the defibrillator.

As previously mentioned, the A wave detector 90 provides a plurality of output pulses for each detected atrial event. Since the activity of the atria is chaotic during atrial fibrillation, it is possible that the A wave detector 90 may provide a continuous stream of closely spaced output pulses for some period of time. Hence, denoting the beginning and end of an atrial event may be difficult under such conditions. As a result, it is preferred that the timer 76 operate so that if an atrial event is wider than a certain time period, for example one hundred milliseconds, then the next output pulse followed by a sample point without a output pulse becomes the end of a current atrial event. The following output pulse becomes the beginning of a new atrial event. Also, if a current output pulse from the A wave detector 90 follows the last immediately preceding output pulse by more than another preset time, for example forty milliseconds, the current output pulse is taken as the beginning of a new atrial event cycle length and the immediately preceding output pulse is taken as the end of the immediately preceding atrial cycle length.

From the foregoing, it can be seen that the present invention precludes atrial fibrillation therapy delivery during cardiac cycles which have normal sinus rhythm characteristics. As a result, the episode log 86 will only contain data reflecting detection and cardioversion of a true atrial arrhythmia such as atrial fibrillation.

While a particular embodiment of the present invention has been shown and described, modifications may be made. For example, the present invention may also be employed to advantage in defibrillators which utilize a bipolar pair of electrodes in the right atrium for sensing atrial activity to support the detection of atrial events and the timing of atrial cycle lengths. It is therefore intended in the appended claims to cover all such changes and modifications which fall within the true spirit and scope of the invention.

What is claimed is:

1. An atrial defibrillator comprising:

means for sensing atrial activity of a heart;

a detector for detecting atrial events from the sensed atrial activity;

a cardioverter for applying cardioverting electrical energy to the atria of the heart when the atria are in need of cardioversion;

means for determining atrial cycle lengths responsive to detected atrial events; and inhibit means for inhibiting the cardioverter from applying the cardioverting energy when an atrial cycle length is greater than a predetermined limit.

2. An atrial defibrillator as defined in claim 1 wherein the predetermined limit is on the order of five hundred milliseconds.

3. An atrial defibrillator as defined in claim 1 further including an atrial fibrillation detector for detecting an atrial arrhythmia requiring cardioversion, a counter for counting atrial cycle lengths greater than the predetermined limit and enable means for causing the atrial fibrillation detector to detect for the atrial arrhythmia when the counter reaches a preselected count.

4. An atrial defibrillator as defined in claim 3 wherein the preselected count is three.

5. An atrial defibrillator as defined in claim 1 wherein the detector includes means for sensing the beginning of each atrial event, and wherein each atrial cycle length begins at the beginning of an atrial event and ends at the beginning of an immediately successive atrial event.

6. An atrial cardioverter comprising:

means for sensing atrial activity of a heart;

an atrial arrhythmia detector responsive to sensed atrial activity for detecting an atrial arrhythmia of the heart;

atrial therapy means for providing atrial therapy to the heart responsive to detection of an atrial arrhythmia; and atrial cycle length determining means responsive to sensed atrial activity for inhibiting the provision of atrial therapy when an atrial cycle length exceeds a predetermined length.

* * * * *